(12) United States Patent
Perrin et al.

(10) Patent No.: US 7,387,031 B1
(45) Date of Patent: Jun. 17, 2008

(54) METHOD FOR MONITORING CORROSION DAMAGE TO A METAL SAMPLE

(75) Inventors: Glenn Perrin, Spring, TX (US); Weyman Dunaway, The Woodlands, TX (US); Thomas S. Carter, Houston, TX (US); Jeffrey McKennis, The Woodlands, TX (US); Surendra K. Mishra, The Woodlands, TX (US); Aaron Ray Morse, Spring, TX (US)

(73) Assignee: Tetra Technologies, Inc., Woodlands, TX (US)

( * ) Notice: Subject to any disclaimer, the term of this patent is extended or adjusted under 35 U.S.C. 154(b) by 0 days.

(21) Appl. No.: 11/644,096

(22) Filed: Dec. 22, 2006

(51) Int. Cl.
  *G01N 3/08* (2006.01)
(52) U.S. Cl. .......................................................... 73/820
(58) Field of Classification Search .................... 73/820
  See application file for complete search history.

(56) References Cited

U.S. PATENT DOCUMENTS

| | | | |
|---|---|---|---|
| 2,873,341 A | 2/1959 | Kutsay | |
| 3,034,340 A | 5/1962 | Jankowsky et al. | |
| 3,067,386 A | 12/1962 | Freedman | |
| 3,400,572 A | 9/1968 | Mizenko | |
| 3,427,873 A | 2/1969 | Mehdizadeh | |
| 3,504,535 A | 4/1970 | Cobb et al. | |
| 4,020,680 A | 5/1977 | Mehdizadeh et al. | |
| 4,135,392 A | 1/1979 | Young | |
| 4,179,940 A | 12/1979 | Oertle et al. | |
| 4,590,804 A | 5/1986 | Brull | |
| 4,639,997 A | 2/1987 | Brull | |
| 4,711,131 A | 12/1987 | Hopkins | |
| 4,812,052 A | 3/1989 | Adam et al. | |
| 5,419,201 A * | 5/1995 | Li et al. ........................ | 73/808 |
| 5,517,851 A | 5/1996 | Berthold et al. | |
| 5,571,955 A | 11/1996 | Beavers et al. | |
| 5,728,943 A | 3/1998 | Colter, Jr. et al. | |
| 5,883,311 A | 3/1999 | Hettiarachchi et al. | |
| 6,789,428 B2 * | 9/2004 | Nishimura et al. ............ | 73/627 |
| 6,912,913 B2 * | 7/2005 | Murakami .................... | 73/808 |
| 6,983,660 B2 * | 1/2006 | Kwon ........................... | 73/806 |
| 7,040,143 B2 * | 5/2006 | Johnson et al. .............. | 73/49.3 |
| 2002/0121370 A1 | 9/2002 | Kurkjian et al. | |
| 2004/0060372 A1 | 4/2004 | Hopkins | |

(Continued)

OTHER PUBLICATIONS

NACE International, Standard Test Method, ANSI/NACE Standard TM0177-96 Item No. 21212, Revised Dec. 23, 1996, 35 pages, Houston, TX, USA.

(Continued)

*Primary Examiner*—Edward Lefkowitz
*Assistant Examiner*—Octavia Davis
(74) *Attorney, Agent, or Firm*—D'Ambrosio & Associates, PLLC

(57) ABSTRACT

A method of monitoring corrosion in a metal sample comprising applying a physical stress to one or more metal samples, placing the metal sample under stress in a sealed vessel, adding one or more fluids to the vessel, measuring the strain on the metal sample over a specified time interval, controlling the environment inside the vessel, calculating the rate of change of the strain measurement over the specified time interval, recording the rate of change of the strain measurement, calculating a moving average of two or more previously recorded rates of change of the strain measurement, and monitoring the moving average to detect damage to the metal sample.

36 Claims, 8 Drawing Sheets

U.S. PATENT DOCUMENTS

2004/0149594 A1    8/2004    Eden
2004/0200295 A1    10/2004    Brossia
2004/0216535 A1    11/2004    Brostmeyer
2005/0050961 A1    3/2005    Tran et al.
2005/0150279 A1    7/2005    Taber et al.

OTHER PUBLICATIONS

ASTM Int'l, Standard Practice for Making and Using C-Ring Stress-Corrosion Test Specimens, ASTM Designation: G 38-01, 8 pages, West Conshohocken, PA, USA.

* cited by examiner

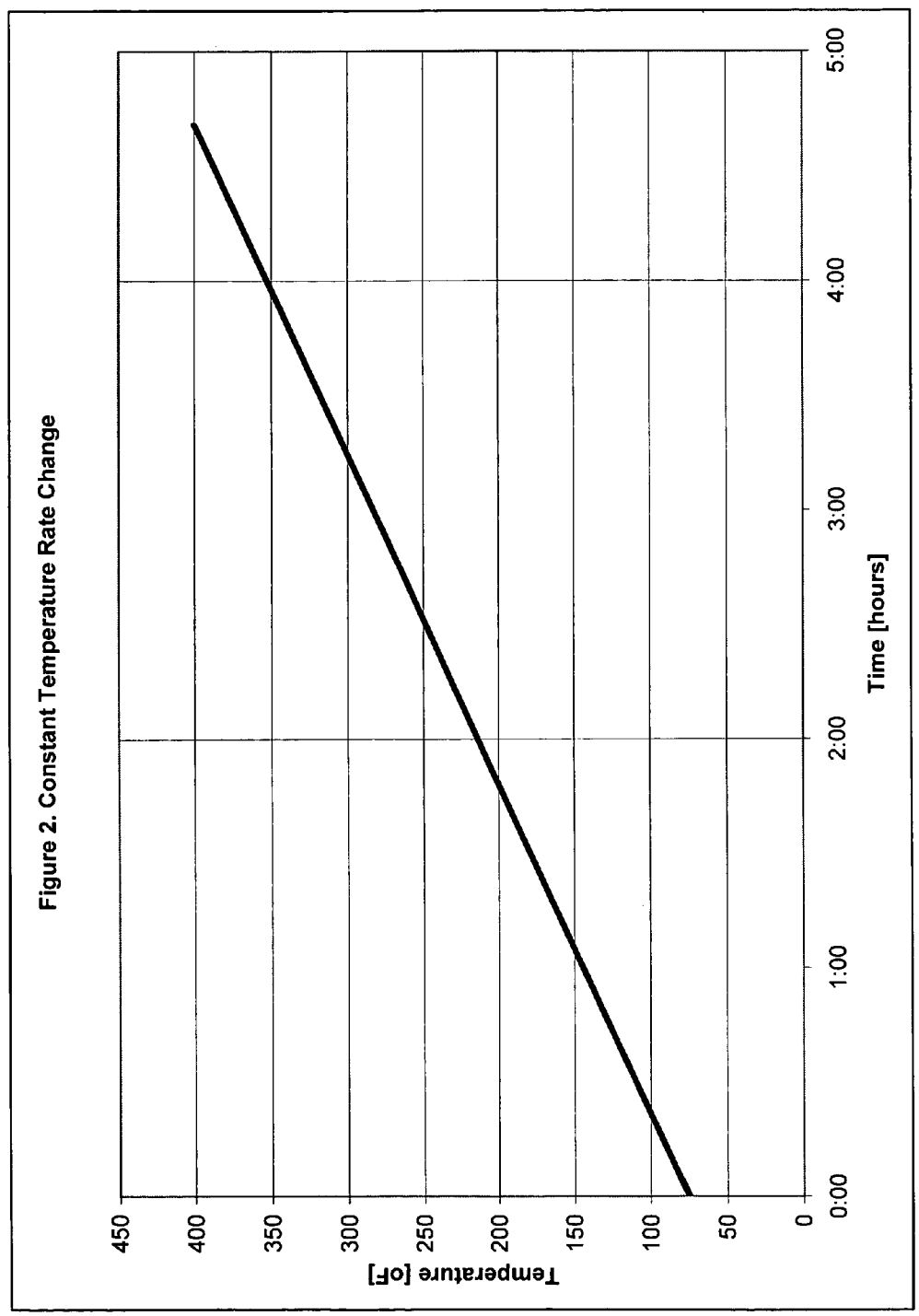
Figure 2. Constant Temperature Rate Change

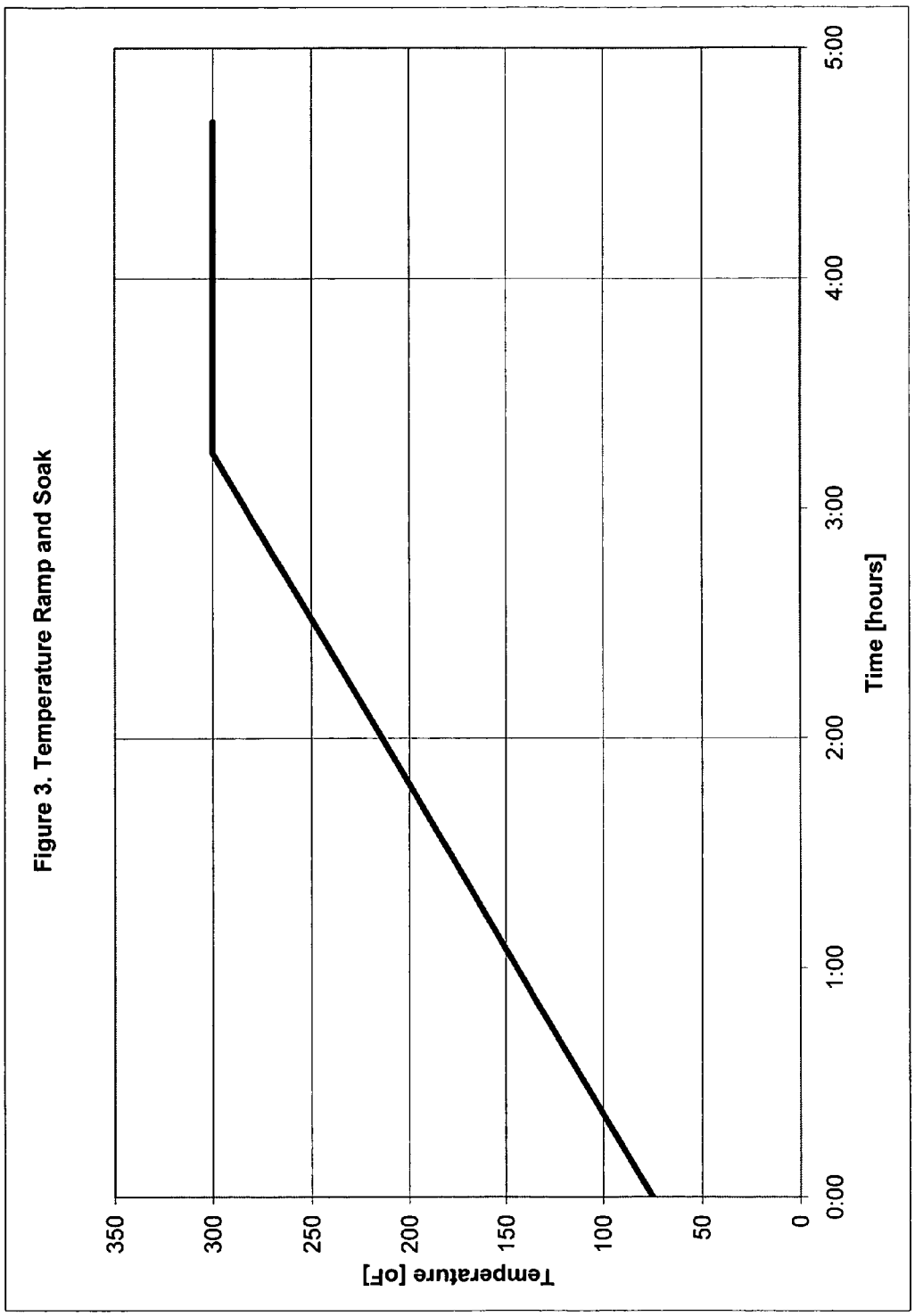
Figure 3. Temperature Ramp and Soak

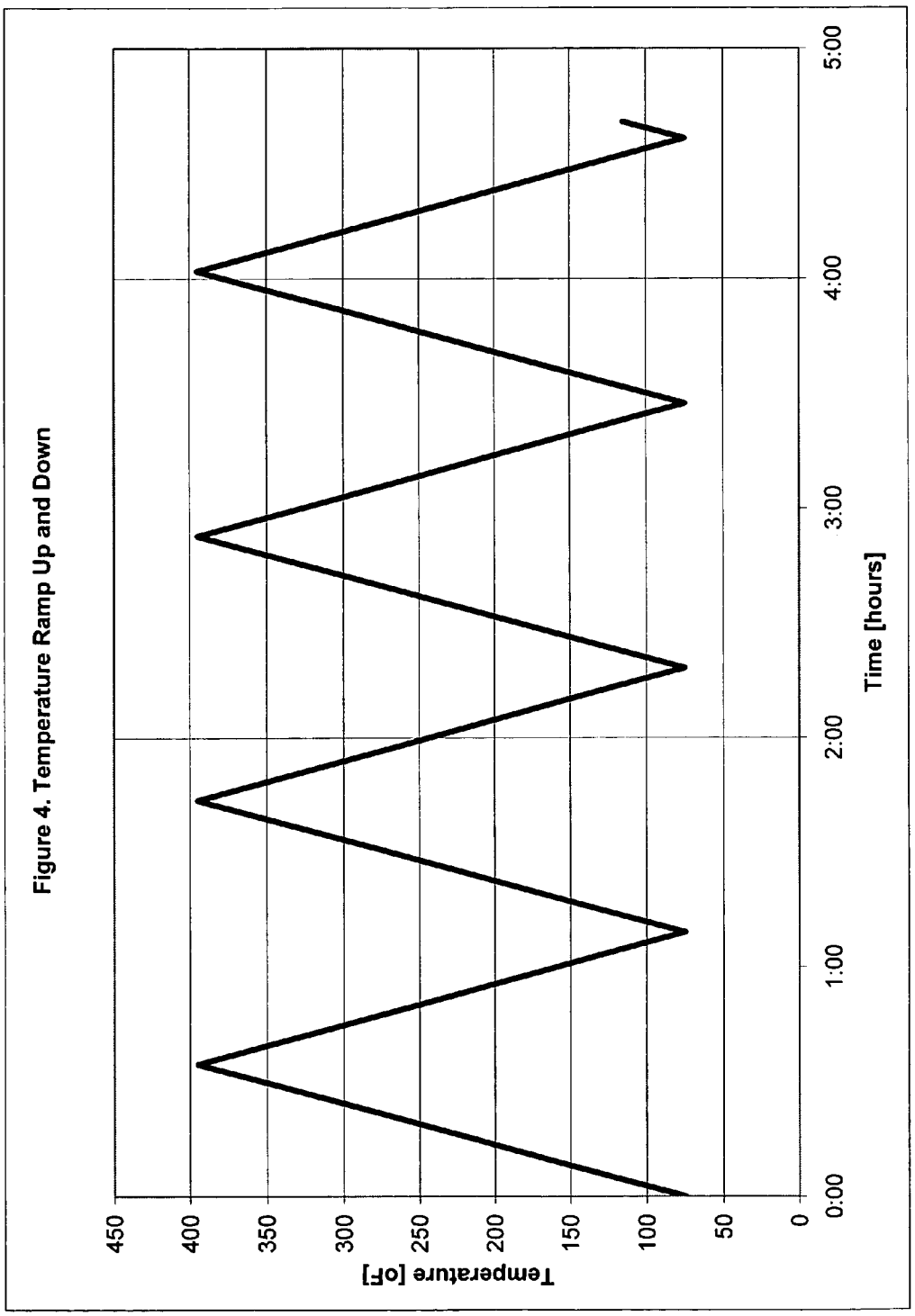

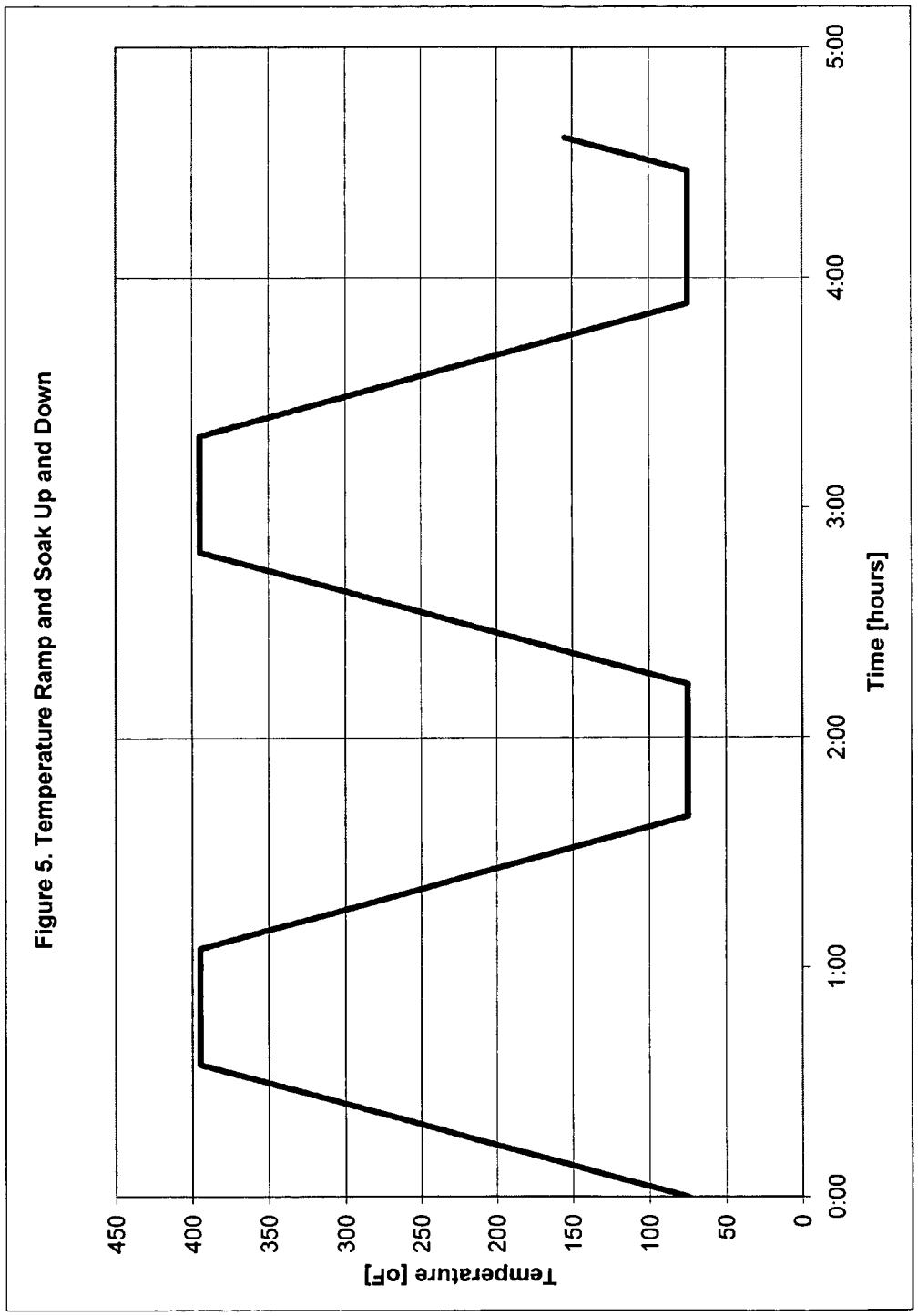

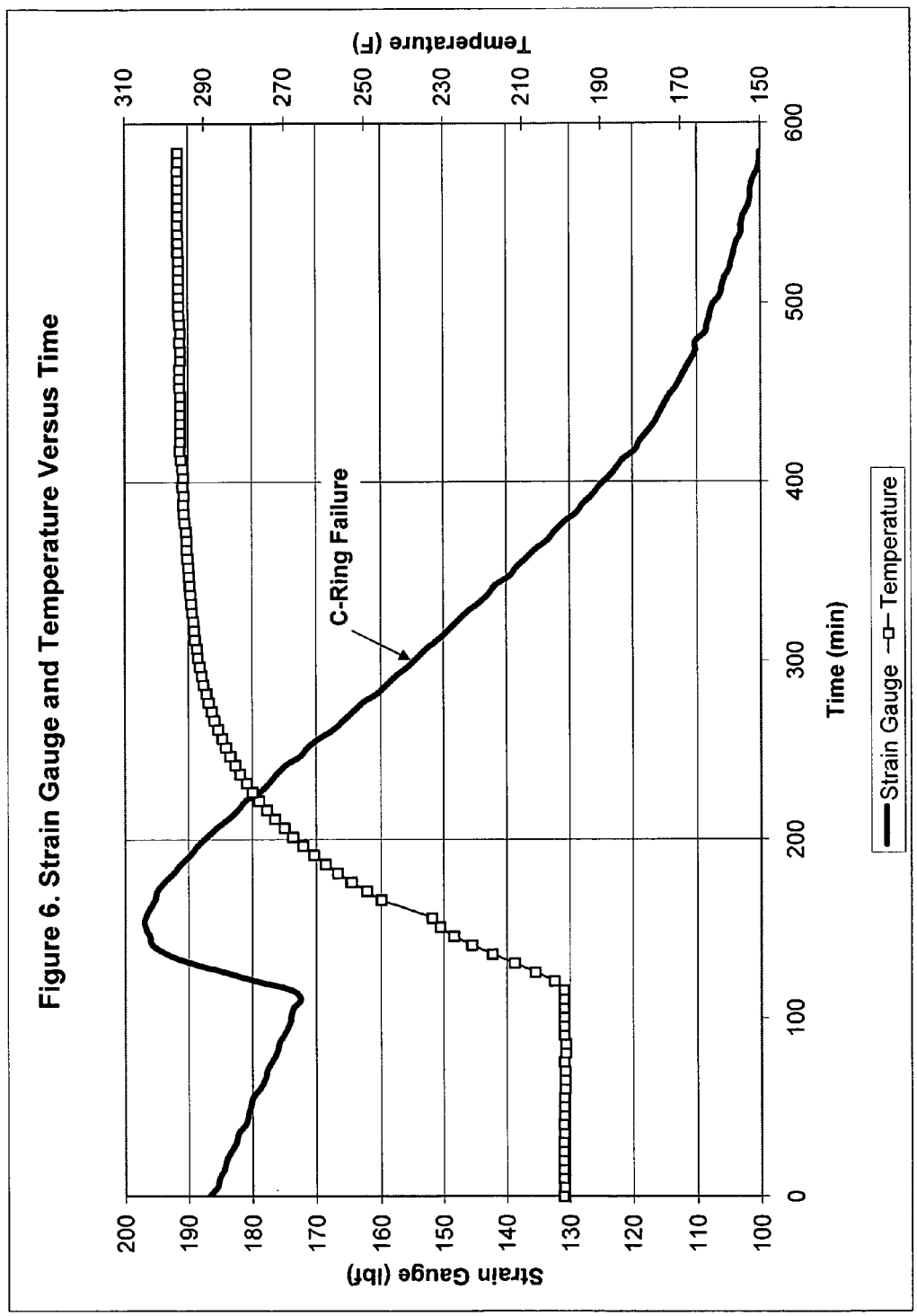
Figure 6. Strain Gauge and Temperature Versus Time

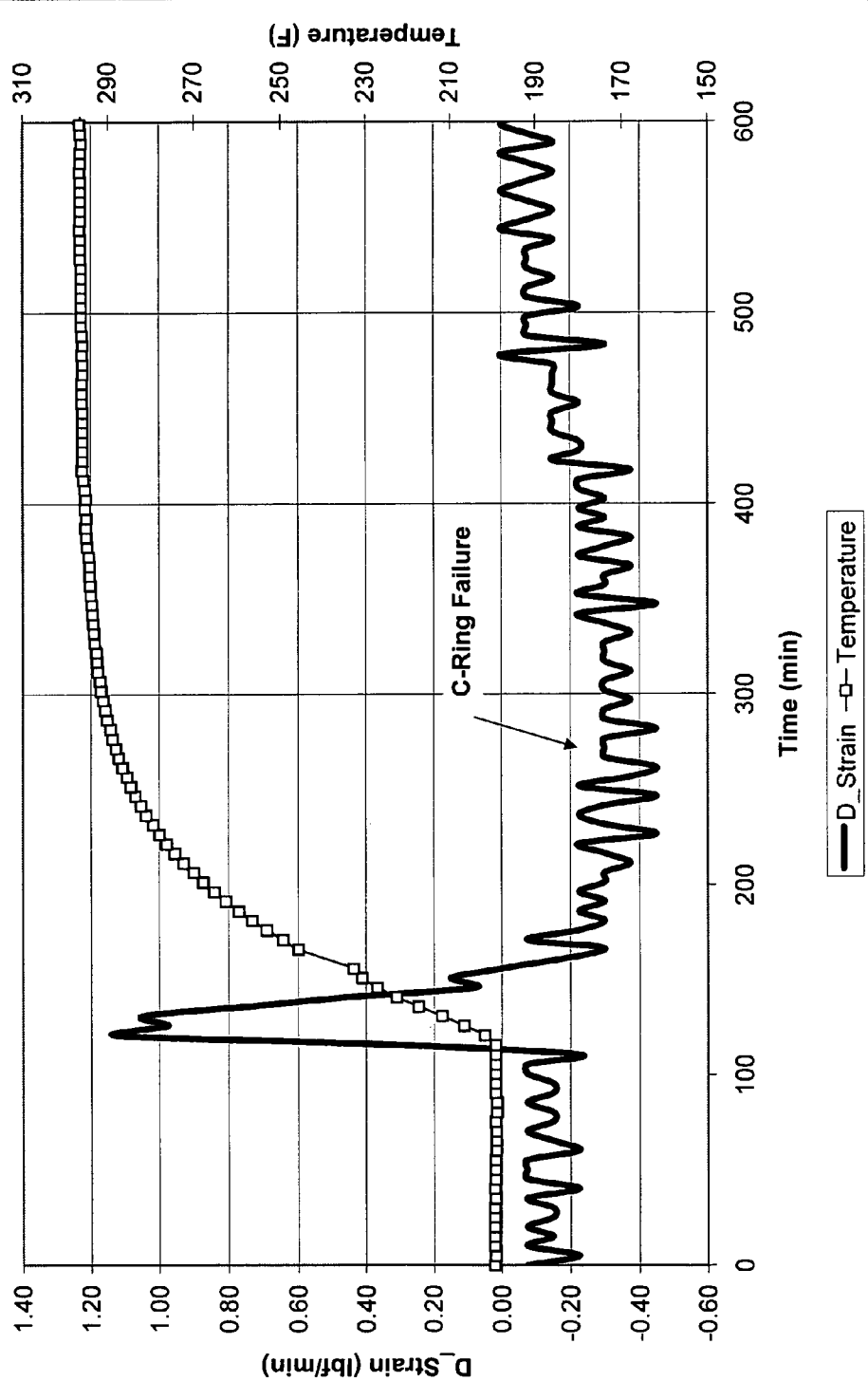

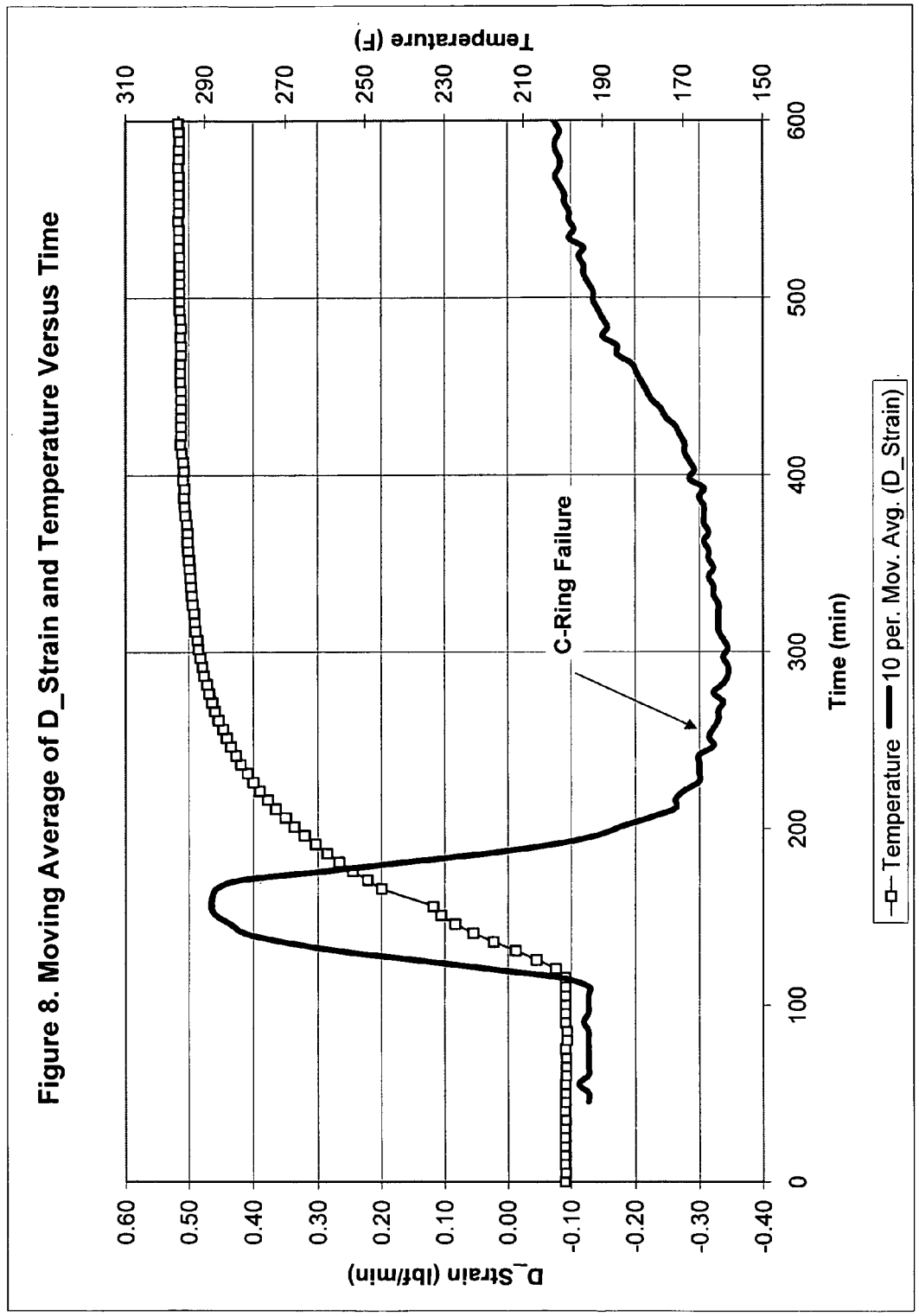

METHOD FOR MONITORING CORROSION DAMAGE TO A METAL SAMPLE

FIELD OF THE INVENTION

The method of this invention relates to monitoring for environmentally induced metal corrosion damage.

BACKGROUND OF THE INVENTION

Metals have a tendency to weaken, corrode, or crack in certain environmental conditions. This problem is prevalent in the oil and gas industry where extreme temperatures, pressures, and chemical environments are often encountered. Testing is often employed to determine what metal alloy is best under the well conditions and to also determine the lifetime of the selected alloy under those conditions.

Environmentally Assisted Cracking

Metal alloys have a yield strength which allows them to withstand a certain amount of yield stress with the occurrence of plastic deformation, but without cracking. Environmental conditions can significantly reduce the amount of force a metal alloy can tolerate, permitting the metal to fail significantly below the yield stress. This phenomenon is generally known as environmentally assisted cracking (EAC). EAC is induced by a combination of three factors: the presence of stress, a corrosive environment, and the sensitivity of the metal to corrosion.

Placing a stress on a corrosion sensitive metal in a corrosive environment comprised of substances such as halides and acidic substances can contribute substantially to EAC. The exact causes of EAC are not fully understood, but exposure to various environmental factors has been shown to be important, for example, temperature, pH, halide concentration, $O_2$ concentration, and the presence of sulfur species such as $H_2S$. Particularly, corrosive environments at high temperatures (e.g. >300° F.) can increase the susceptibility of a metal to EAC.

Individual metals and alloys react uniquely to environmental conditions. Therefore, it is important to test a metal under the conditions it will be used. EAC is a common problem in the oil and gas industry as corrosive chemicals and metals under high stress at extreme temperatures are frequently encountered in underground wells and deep sea drilling. In view of the expense of completing and producing a well, the metals and fluids used in these phases are carefully selected based on testing. Unexpected metal failures are both expensive to correct and potentially dangerous. Clearly, it is most important that such testing be conducted under conditions simulating those of the well.

NACE Tests

The National Association of Corrosion Engineers (NACE) has developed a standard test method (NACE TMO 177-96 Method C) for laboratory testing a metal's resistance to Environmental Cracking, EC. This type of testing is more commonly referred to as Environmentally Assisted Cracking, EAC.

The NACE method involves placing a stressed sample of the metal in a test vessel under corrosive conditions. The test specimen is a "C" shaped piece of material known as a C-ring. NACE standardizes the specific measurements of the C-ring.

The NACE C-ring includes two holes through which a bolt passes. The bolt is tightened on either end to apply a stress to the C-ring. To ensure that the proper amount of stress is applied to the C-ring, an electrical resistance strain gauge is used to measure strain in the C-ring at the time the bolt is tightened.

The bolt is tightened until the appropriate strain gauge reading is achieved. NACE specifies that the strain gauge is placed on the outside diameter at a point 900 opposite the axis of the bolt. After the tightening the bolt, both the strain gauge and the glue used to adhere the gauge to the C-ring must be removed. Once the strain gauge is removed, the C-ring and bolt are then cleaned and placed in the vessel for testing. NACE specifies that $H_2S$ is added to the vessel and the test is run for up to 720 hours with no provision for detecting early failure.

NACE also specifies that EAC is detected by removing the C-ring from the vessel and searching for cracking by visually examining the specimen. Since cracking cannot be observed while the test is in progress, tests often run much longer than required. Additionally, determination of alloy lifetime takes multiple tests since the test must be repeatedly stopped and restarted to determine if failure has occurred. Therefore, reliable real time observation of specimen corrosion damage is preferable.

Strain Gauge

As in the NACE method, strain on an object is an indicator of stress within the object. Strain is defined as the amount of deformation per unit length of an object when a load is applied. When a load is applied to a wire it undergoes strain, lengthening slightly. The strain causes a change in the electrical resistance of the wire. A strain gauge measures strain by measuring the wire's resistance.

Generally, the strain gauge is mounted to an object under strain with an adhesive and deforms with the object. The strain gauge is comprised of wires which stretch and change electrical resistance as the object deforms. A measure of the strain gauge resistance change correlates to the strain occurring in the object to which the strain gauge is attached.

Temperature is known to affect strain gauge measurements. The measured strain will tend to drift as the temperature of the strain gauge changes. The drift associated with the temperature of the strain gauge makes strain measurements at changing temperatures difficult to interpret. Therefore, it is important to compensate for temperature's effect on the strain measurement.

Background Methods

In general, the NACE method is used to test for corrosion damage in a C-ring specimen. The NACE apparatus allows the C-ring specimen to be compressed in an assembly. The force of the compression load is calibrated with strain gauges temporarily mounted on the outside surface of the C-ring arc. In the NACE method, the strain gauges are removed after calibration and are not used in the direct measurement of the corrosion damage. The strain gauges must be removed before the specimen is placed in the test chamber. After a prolonged testing period, the test is halted and the C-ring visually inspected to determine if EAC occurred. Unfortunately, with the NACE method, a real time reading of the strain in the C-ring assembly is not possible.

Several methods of real-time monitoring of strain in a metal component have been developed. In the previous methods of testing metal samples, real time monitoring of corrosion damage to the metal sample consisted of plotting strain measurements and visually monitoring the strain measurement to detect sample failure. Noise in the strain gauge signal and drift in the strain measurement due to environmental conditions, such as temperature, make it difficult to accurately determine when failure occurs based on the strain measurement.

Additionally, previous methods did not enable sensitive real-time monitoring of localized corrosion events such as pitting that often precede EAC, as well as the EAC event itself. Also, a means to determine the causative factors associated with the corrosive event, be it EAC, pitting, etc., by correlation to the time of the event's occurrence was not available.

Given the numerous variables that influence environmentally assisted cracking, sample corrosion damage, and variation of strain measurements, a method of measuring strain during the testing for corrosive damage to the metal sample that provides greater accuracy in corrosion damage measurement is desirable. A method which also provides the ability to monitor localized corrosion real-time and correlate the causative factors of corrosion with sample failure events is also desirable.

SUMMARY OF THE INVENTION

The method of this invention, allows for real-time monitoring of damage to a metal sample. The method includes monitoring the moving average of the rate of change of strain in the metal sample, which indicates damage to the metal sample while removing noise from strain data. With this method, the time requisite for the corrosion damage to a metal sample is more precisely defined than in previous methods. Monitoring the moving average rather than the individual values decreases the amount of variation in the monitored value. The moving average value compensates for noise and temperature induced drift in the strain measurement as the rate of change. Thus, the reliability of indications of corrosion damage to the metal sample is increased by monitoring the moving average.

In one embodiment, the method of this invention comprises, applying a physical stress to one or more metal samples, placing the metal sample under stress in a sealed vessel, adding one or more fluids to the vessel, measuring the strain on the metal sample over a specified time interval, controlling the environment inside the vessel, calculating the rate of change of the strain measurement over the specified time interval, recording the rate of change of the strain measurement, calculating a moving average of two or more previously recorded rates of change of the strain measurement, and monitoring the moving average to detect damage to the metal sample.

In another embodiment, the electrochemical properties of the fluid in the vessel can be monitored. The electrochemical properties can be correlated to the strain data to determine electrochemical indicators of corrosion of the metal sample.

Additionally, the identification of the key parameters associated with the damage, such as temperature, pH and chemical composition, can be obtained and correlated to damage indicators. With such information, mechanistic information regarding the corrosion event can be gleaned. Greater accuracy in discovering a metal's stress limits under harsh environmental conditions results in improved selection of metals used in a variety of applications, especially in tubing and other downhole metal equipment.

BRIEF DESCRIPTION OF THE DRAWINGS

FIG. 2 is an example of temperature changing at a constant rate versus time.

FIG. 3 is an example of temperature ramp and soak.

FIG. 4 is an example of temperature ramping up and down.

FIG. 5 is an example of temperature ramp and soak up and down.

FIG. 6 is graph of measured strain and temperature v. time.

FIG. 7 is graph of the rate of change of the strain and temperature v. time.

FIG. 8 is graph of a moving average of the rate of change of strain and temperature v. time.

DETAILED DESCRIPTION

The method of this invention allows damage to a metal sample to be monitored real-time by measuring and tracking a moving average of the rate of change strain within the metal sample. The metal sample is placed under physical stress in a controlled environment and strain within the sample is monitored to determine when the metal sample is losing resistance the physical stress.

In a first embodiment, the method for monitoring damage to one or more metal samples comprises stressing the metal sample, placing the sample in a sealed vessel, adding one or more fluids to the vessel, measuring the strain on the metal sample over a specified time interval, controlling the environment inside the vessel, calculating the rate of change of the strain measurement over the specified time interval, recording the rate of change of the strain measurement, calculating a moving average of two or more previously recorded rates of change of the strain measurement, and monitoring the moving average to detect damage to the metal sample.

Figure 1A:
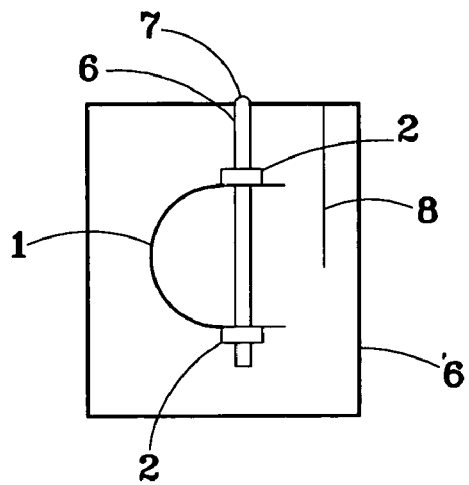
FIG. 1A is a side view of one embodiment of the apparatus used in the method of this invention.

Referring to FIG. 1A, an example of an apparatus that may be used to perform the method of this invention is shown. In one aspect of the method, a physical stress is applied to the metal sample. In the application of this method, any type of physical stress may be applied to sample. In various embodiments, the physical stress can include a compressive force, a tensile force, a hoop stress, a torsion stress, or a combination of any of these stresses.

In one embodiment, the stress is applied to the metal sample by placing a rod through holes in the metal sample 1 and compressing the metal sample between two bracing means 2 positioned on the rod 6. The bracing means are tightened with a wrench to compress the metal sample 1. The stress on the metal sample is measured with a strain gauge 1 placed inside the rod 6. The strain gauge is electrically connected to a computer which records the stress measured by the strain gauge and manipulates the recorded data.

The metal sample 1 may have any suitable shape. In one embodiment, the metal sample 1 is C-shaped. Examples other of suitable shapes include but are not limited to rectangular, circular, cylindrical, and L-shaped.

Figure 1B:
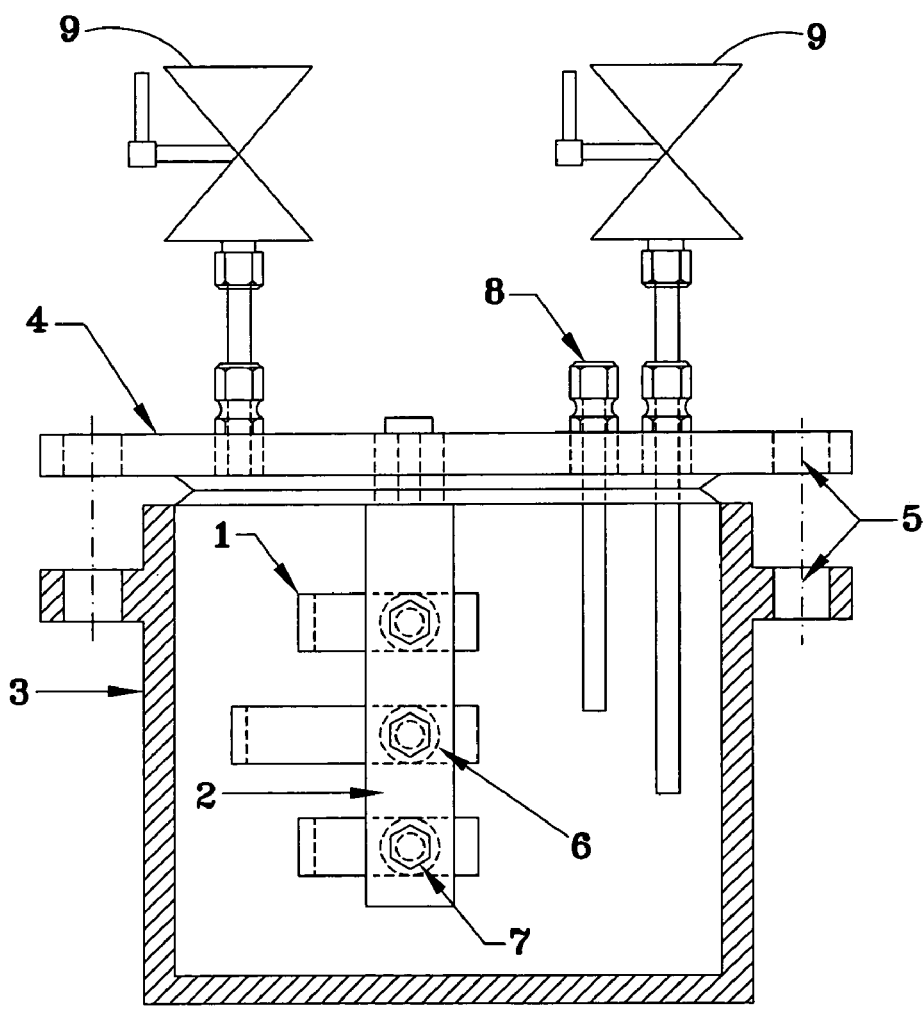
FIG. 1B is a sectional view of an example EAC Tester assembly.

Referring now to FIG. 1B, another example of an apparatus that may be used in the method of this invention is shown. The metal sample 1 is stressed by compressing the sample between bracing means 2 positioned on the rod 6. To allow multiple samples to be tested simultaneously, one of the bracing means 2 can comprise a rack. The rack having multiple holes through which rods 6 can be placed. In this way, several samples can be tested. Testing multiple samples can decease the cost of running multiple tests. It also allows confirmation of the test data with multiple test samples.

The metal sample 1 under stress is placed in a sealed vessel 3. One or more fluids are added to the vessel 3. The environment inside the vessel 3 is controlled. To detect corrosion damage to the metal sample 1, strain on the metal sample 1 is measured. In one embodiment, the sealable vessel 3 is a pressure vessel of any of several corrosion resistant metallurgies known in the art. The vessel has a removable lid 4 which bolts shut 5 to seal the vessel 3.

The stress on the metal sample is measured with a strain gauge. Suitable types of strain gauges include electrical strain gauges or fiber optic strain gauges. The strain gauges can be positioned in any position where they are capable of measuring stress on the metal sample. In one embodiment, the strain gauge 7 is positioned inside the rod 6 within the vessel. In further embodiments, the strain gauges are positioned on the rod, on the metal sample, or outside the vessel.

Vessel Environment

To test for corrosion damage to the metal sample, the environment inside the vessel is controlled. The environmental control factors can include the temperature, pressure, and fluid composition within the vessel.

In one embodiment, the temperature inside the vessel 3 is controlled by placing a temperature probe 8 inside the vessel 3 to measure the temperature within the vessel. The temperature probe 8 transmits the temperature measurement to a control system. The control system then controls an external source of heat or refrigeration in response to the temperature measurement inside the vessel. In another embodiment, the external source of heat is an oven, inside of which the vessel 3 is positioned.

Pressure levels inside the vessel can also be controlled by admitting or withdrawing fluids to the vessel through the valves 9. For the purposes of this invention, a fluid is defined as any liquid, gas or solid suspension.

The chemical composition of the environment inside the vessel is also controlled to test the metal sample. In the method of this invention, any combination of fluids can be added to the vessel to control the chemical composition inside the vessel. Often the fluids added will represent a simulation of the fluids present downhole in an oil or gas well. Examples of fluids which may be added to the vessel to form the environment include acids, oxygen, hydrogen sulfide, carbon dioxide. Simulation of the well conditions tests the metal's strength under working conditions. The simulation allows metal piping and equipment with a predictable lifetime under the conditions of use to be selected.

Additives can also be introduced into the vessel to determine how the additives affect the lifetime of the metal in the fluid environment. Examples of additives include chemical corrosion inhibitors, biocides, oxygen scavengers, buffered chemicals, and performance modifiers. A performance modifier is any substance that affects the lifetime of the metal sample in the fluid environment. Including additives in the vessel's fluid environment allows for the selection of additives that will increase the metal's lifetime under the environmental conditions simulated in the vessel.

Detection of Corrosion Damage

In one embodiment of the method of this invention, corrosion damage to the metal sample 1 is detected by monitoring the strain on the metal sample. Strain on the metal sample 1 is measured over a specified time interval. The rate of change of the strain measurement over the specified time interval is calculated and recorded. The rate of change of the strain gauge measurement or differential strain (D_Strain) is calculated by subtracting the previous strain measurement from the most recent strain measurement and dividing this difference by the time between the two strain measurements, as shown in the equation below:

$$D\_Strain_1 = (Strain_2 - Strain_1)/(time_2 - time_1)$$

A moving average of the recorded rates of change of the strain measurement is then calculated and monitored to detect corrosion damage to the metal sample. The moving average of the rate of change of the strain measurement is calculated by summing a certain number of rates of change records and dividing the sum by the number of records summed. For the purposes of this invention, any number of records may be averaged. However, in some cases averaging 10 records produces a moving average value that can be reliably monitored. The general equation for calculating a moving average of an arbitrary number records, N, is shown below:

$$D\_Strain_{Moving\ average} = (D\_Strain_1 + D\_Strain_2 + \ldots D\_Strain_N)/N$$

The value of the moving average of the rate of change of the strain gauge measurement, differential strain, indicates that damage to the metal sample occurred. For example, a sudden decrease in the moving average indicates that metal sample is losing resistance to the stress applied by the bracing means. A loss of resistance is a sign that the metal sample is bending or cracking due to temperature stress, chemical stress, or physical stress applied to the metal sample. A change in resistance may also signal the occurrence of pitting or other pre-cracking localized corrosion.

The benefit of monitoring the moving average of several differential strain records is that noise in the data, such as electrical transients, is filtered out thereby giving a more reliable indicator of damage to the metal sample. FIG. 6, FIG. 7, and FIG. 8 are graphs for different indicators for the same corrosion test data. In the test, actual failure of the metal sample occurred between 225 minutes and 300 minutes. FIG. 6 is a graph of the strain gauge measurement over time. Monitoring of strain alone for an indication of sample damage is difficult. In FIG. 6, the reader could only determine that the failure occurred sometime between 150 min. and 500 min. There is no indication in the strain measurement graph that indicates a failure actually occurred between 225 and 300 minutes. FIG. 7 is a graph of the rate of change of strain over time for the same strain data as shown in FIG. 6. The rate of change of strain becomes negative at about time 150 min., an indication that strain is dropping and the sample may be failing. However, the rate of change fluctuates up and down. This noise makes it difficult for the viewer to determine whether failure of the sample has actually occurred and when the failure begins and ends. FIG. 8 is a graph of a moving average of the prior ten rate of change data points from FIG. 7. The moving average does not fluctuate to the degree of rate of change alone. The noise shown in FIG. 7 is greatly reduced, making determination of failure by the reader more accurate. The reader can determine that the failure of the sample occurred between times 225 and 300. Between these times strain dropped at the highest rate, about −0.30 lbf/min, before returning to 0.0 lbf/min, no change in strain.

The moving average can be monitored in any suitable manner to determine if and when damage to the sample has occurred. Suitable manners of monitoring the moving average to detect damage include, but are not limited to, visually monitoring a plot of the moving average or programming an electronic device to compare the moving average to predetermined value to indicate corrosion damage.

Monitoring Vessel Environment

In an additional embodiment of the method of this invention, the internal environment of the vessel is monitored. The environmental factors which can be monitored include the pH of the fluid inside the vessel, the chemical composition of the fluid inside the vessel, the pressure inside the vessel, and the electrochemical properties of the fluid in the vessel. These factors each may contribute to an increase of decrease in the corrosion of metal. During the method of this invention, various factors can be manipulated to determine how the combination of factors affects failure of the metal sample. The pH level of the fluid is measured by placing a pH probe inside the vessel. Alternatively, the samples of the fluid inside the vessel can be drawn from the vessel and pH level of those samples measured.

The chemical composition of the fluid can also be monitored in several ways. In one embodiment, the chemical composition is monitored by placing an ion selective electrode in the vessel. An ion selective electrode is defined as any electrode designed to monitor the concentrations of target cations or anions.

Alternatively, a sample of the fluid in the vessel can be drawn and the chemical composition of the sample determined by using chemical testing methods known in the art.

The occasions at which measurements of the internal environment of the vessel are taken may be arbitrary. However, the occasions may also be based on a predetermined plan or triggered by another measured value of the vessel or metal sample. In one embodiment, the pressure inside the vessel is measured and the rate of change of the pressure is calculated. When the rate of change exceeds a predetermined limit, a sample of the fluid is drawn. Alternatively, a sample of the fluid can be drawn when the rate of change of the strain measurement of the metal sample exceeds a predetermined limit. Once the fluid sample is drawn, measurement of the pH level in sample and analysis of the chemical composition of the sample can be performed.

In a further embodiment of the method of this invention, the ion selective electrode is used to detect corrosion damage to the metal sample. A chemical species whose presence in the fluid is known to indicate corrosion damage to the metal sample is tracked. The ion selective electrode is selected to measure the amount of a specific chemical species in the fluid. The level of the chemical species in the fluid is tracked by a computer or another tracking means. A sudden change in the measured level of the chemical species in the fluid indicates corrosion damage to the metal sample.

In still another embodiment of the method, the electrochemical properties of the fluid in the vessel can also be monitored. Electrochemical probes are placed in a vessel and one or more electrochemical properties of the fluid are measured. Electrochemical properties that can be measured include potential (voltage), current, and resistance. Frequently, one property is monitored as another is varied. For example, current can be measured as a function of change in potential with a potentiostat.

Corrosion of the metal sample can occur uniformly over the entire sample or corrosion can be localized in a few areas. Localized corrosion is also known as pitting. Electrochemical monitoring can detect both types of corrosion through detection of changes in the properties of the fluid that occur as metal is consumed in the corrosion reaction. The data collected during electrochemical monitoring can be correlated with the strain gauge measurement to allow the user to understand what electrochemical properties serve as an indicator of corrosion of the metal. Various techniques, such as linear polarization resistance, harmonic distortion analysis, or electrochemical noise are then used to transform the data into useful general or localized corrosion information.

In one embodiment, the monitoring of general or uniform corrosion damage within the vessel environment, with a technique such as by linear polarization resistance (LPR), is performed by insertion of selected electrochemical probes into the vessel. In another embodiment, localized corrosion such as pitting is electrochemically monitored in real time. The electrochemical pitting data is then correlated with changes in the strain gauge measurements.

Temperature Testing

In the method of this invention, temperature's effect on the metal sample can also be tested. The temperature inside the vessel may be either held constant or changed in various ways. The adjustment of the temperature may be performed manually or preprogrammed into a computer or another type of control system, such as a programmable logic controller. As shown in FIG. 2, in one embodiment of the method, the temperature inside the vessel is changed at a constant rate. The temperature is either increased or decreased at this rate. This embodiment of the method can be employed to determine, in a single test, at what temperature corrosion damage to a metal sample causes the sample to begin to fail.

In another embodiment of the method, the temperature inside the vessel is changed at a constant rate until the temperate reaches a predetermined temperature. A graph illustrating this embodiment of the method is shown in FIG. 3. When the vessel reaches the predetermined temperature, the temperature is maintained for a period of time. The period of time can be either predetermined or last until sample failure is detected.

In yet another embodiment, the temperature inside the vessel is periodically changed. The periodic change may be in the form of cyclic increase and decrease of the temperate inside the vessel, as shown in FIG. 4. The periodic change may also be in the form a step-wise periodic increase or decrease in temperature, as shown in FIG. 5. In a step-wise periodic change, the temperature is changed to a predetermined temperature and then maintained for a period of time before being changed again. Temperature changes may be performed by simply changing the temperature set point and allowing the source of heat or refrigeration to make the temperature change occur as fast as possible.

Temperature Compensation

When a strain gauge is used to measure the strain on the metal sample, a changing temperature is known to affect the measurement. The measured strain on the metal sample will tend to drift as the temperature of the strain gauge changes. A change in the strain measurement normally indicates that the metal sample is corrosion damaged. However, the drift associated with the changing temperature of the strain gauge makes monitoring the strain measurement difficult to interpret. Therefore, when monitoring the corrosion damage to the metal sample, it is important to compensate for temperature's effect on the strain measurement. Otherwise, the false readings could indicate corrosion damage to the sample where none is present.

In one embodiment of the method of this invention, temperature is measured and recorded at the time when strain measurements are taken. Corrosion damage to the metal sample may be detected by monitoring a ratio of the differential strain to differential temperature (D_Strain/D_Temp), which is calculated by dividing the change in strain measurement by the change in the temperature measurements over the same period of time. Calculation of the ratio is illustrated in the following equation:

$$D\_Strain/D\_Temp = (Strain_2 - Strain_1)/(Temp_2 - Temp_1)$$

To compensate for the strain measurement fluctuation caused by temperature changes the calculated ratio, D_Strain/D_Temp, may be compared to a ratio of baseline values. The baseline values are gathered by preparing a sample of the same metal and performing the same test with an inert environment inside the vessel. Since the internal environment of vessel is inert, the metal sample is not subject to chemical attack and any changes in strain measurements are caused by temperature alone. In the actual test, the fluids in the vessel will influence the strain measurement by damaging the metal sample.

To determine which changes in the strain measurement are due to temperature and which are due to corrosion damage of the metal sample, the actual test data is compared to the baseline strain measurement data at the same temperature in one of two ways. First, the difference between the baseline data and the actual data at the same temperature may be calculated by subtracting the baseline ratio from a ratio of the actual test over the same temperature interval. The difference can then be monitored to detect corrosion damage to the metal sample. In a second alternative, the actual test data ratio's percentage of the baseline ratio at the same temperature may be calculated to indicate which strain measurement changes are due to temperature and which are due to sample corrosion damage. The percentage of the baseline ratio is calculated by dividing the test ratio by the baseline ratio. The percentage can then be monitored to detect corrosion damage to the metal sample. Monitoring of the sample may be performed either by plotting the value and visually watching for substantial changes or by programming a computer to compare the value to a predetermined value and generate a signal when the calculated value reaches the predetermined percentage value.

In another embodiment, temperature compensation may alternatively be achieved by placing a second set of one or more metal samples inside the oven, but outside the vessel. In this manner, the second set of metal samples will experience the same temperature effects as the first sample, but not the effects of the fluid environment in the vessel. A physical stress is applied to the second set of metal samples to match the stress of the first set. The stress on the second set will also be measured with a strain gauge. The signal from this second set strain gauge is subtracted from the strain gauge signal inside the vessel to compensate for the temperature effects on the strain gauge measurement. The difference is then monitored to detect strain.

While certain embodiments and details have been shown for the purpose of illustrating this invention, it will be apparent to those skilled in the art that various changes and modifications may be made herein without departing from the spirit or scope of the invention.

The invention claimed is:

1. A method for monitoring for damage to a metal sample comprising:
   (a) applying a physical stress to one or more metal samples;
   (b) placing the metal sample under stress into a sealed vessel;
   (c) adding one or more fluids to the vessel;
   (d) measuring the strain on the metal sample over a specified time interval;
   (e) controlling the environment inside the vessel;
   (f) calculating the rate of change of the strain measurement over the specified time interval;
   (g) recording the rate of change of the strain measurement;
   (h) calculating a moving average of two or more previously recorded rates of change of the strain measurement; and
   (i) monitoring the moving average to detect damage to the metal sample.

2. The method of claim 1 wherein the fluid is a downhole fluid.

3. The method of claim 1 further comprising adding one or more additives to the vessel, the one or more additives selected from chemical corrosion inhibitors, biocides, oxygen scavengers, buffered chemicals, acids, hydrogen sulfide, carbon dioxide, performance modifiers, and combinations thereof.

4. The method of claim 1 wherein strain is measured with a strain gauge.

5. The method of claim 1 wherein applying a physical stress to the metal sample is performed by applying a compressive force to the metal sample, applying a tensile force to the metal sample, applying a hoop stress to the metal sample, or applying a torsion stress to the metal sample.

6. The method of claim 1 wherein the step of applying a physical stress to the metal sample comprises the steps of:
   placing a rod through one or more holes defined in the metal sample; and
   compressing the metal sample with one or more bracing means positioned on the rod.

7. The method of claim 1 further comprising:
   periodically changing the temperature inside the vessel.

8. The method of claim 1 further comprising:
   changing the temperature inside the vessel at a constant rate.

9. The method of claim 8 further comprising:
   changing the temperature inside the vessel at a constant rate until the temperature reaches a predetermined temperature; and
   maintaining the temperature inside the vessel at the predetermined temperature.

10. The method of claim 1 further comprising increasing and decreasing the temperature inside the vessel in a periodic manner.

11. The method of claim 1 further comprising:
    controlling the temperature inside the vessel;
    measuring the temperature inside the vessel;
    calculating the change of the temperature inside the vessel over the time interval;
    calculating a ratio of differential strain to differential temperature by dividing the change of the strain measurement over the time interval by the change in temperature over the time interval; and
    monitoring the ratio to detect damage of the metal sample.

12. The method of claim 11 further comprising:
    developing a baseline strain data set for the metal sample at different temperatures;
    calculating a comparison value of the ratio of differential strain to differential temperature to the baseline strain data; and
    monitoring the comparison value to detect damage to the metal sample.

13. The method of claim 12 wherein the comparison value is calculated by a step selected from a group consisting of: calculating a ratio of the ratio of differential strain to differential temperature to a ratio of differential baseline strain to differential temperature, and calculating the difference between the ratio of differential strain to differential temperature and a ratio of differential baseline strain to differential temperature.

14. The method of claim 1 wherein step (f) further comprises
    applying a physical stress to a second set of one or more metal sample;
    placing the second set of metal samples outside the sealed vessel;

controlling the temperature of the second set of metal samples to match the temperature of the metal samples inside the vessel;

measuring the strain on the second set of metal samples over the specified time interval;

calculating a temperature compensated strain measurement by subtracting strain measurement of the second metal sample from the strain measurement of the first metal sample; and calculating the rate of change of the strain measurement over the specified time interval using the temperature compensated strain measurement.

15. The method of claim 1 wherein the method further comprises the step of:

monitoring the pH of the fluid inside the vessel.

16. The method of claim 1 wherein the method further comprises the step of:

monitoring the chemical composition of the fluid inside the vessel.

17. The method of claim 16 wherein the step of monitoring the chemical composition of the fluid inside the vessel comprises placing an ion selective electrode in the vessel.

18. The method of claim 16 wherein the step of monitoring the chemical composition of the fluid inside the vessel comprises monitoring one or more electrochemical properties of the fluid in the vessel.

19. The method of claim 18 further comprising correlating changes in the electrochemical properties of the fluid with changes in the moving average of the strain measurement to determine electrochemical indicators of damage to the metal sample.

20. The method of claim 18 further comprising:

detecting changes in the electrochemical properties of the fluid in the vessel to indicate damage to the metal sample.

21. The method of claim 18 further comprising:

sampling the fluid inside the vessel when one or more electrochemical properties of the fluid reaches a predetermined value.

22. The method of claim 1 further comprising:

sampling the fluid in the vessel.

23. The method of claim 22 further comprising:

measuring the pressure inside the vessel;

calculating the rate of change of the pressure inside the vessel; and drawing a sample of the fluid inside the vessel when the rate of change of the pressure inside the vessel exceeds a predetermined limit.

24. The method of claim 22 further comprising:

sampling the fluid inside the vessel when the recorded rate of change of the strain measurement exceeds a predetermined limit.

25. The method of claim 22 further comprising a one or more steps selected from: measuring the pH of the sample and analyzing the chemical composition of the sample.

26. The method of claim 1 wherein the moving average is calculated by averaging the last ten recorded rates of change of the strain measurement.

27. The method of claim 1 wherein the step of monitoring the moving average to detect damage to the metal sample comprises:

plotting the moving average; and visually monitoring the plot of the moving average for sudden shifts that indicate damage to the metal sample.

28. The method of claim 1 wherein the step of monitoring the moving average to detect damage to the metal sample comprises:

comparing the moving average to a predetermined moving average value; and indicating damage to the metal sample when the moving average reaches the predetermined moving average value.

29. A method for monitoring for damage to a metal sample comprising:

(a) applying a physical stress to a metal sample;

(b) placing the metal sample under stress into a sealed vessel;

(c) adding one or more fluids to the vessel;

(d) measuring the strain on the metal sample over a specified time interval;

(e) controlling the environment inside the vessel;

(f) calculating the rate of change of the strain measurement over the specified time interval;

(g) recording the rate of change of the strain measurement;

(h) calculating a moving average of two or more previously recorded rates of change of the strain measurement; and (i) monitoring the moving average to detect damage to the metal sample by plotting the moving average and visually monitoring the plot of the moving average for changes in the moving average that indicate damage to the metal sample.

30. The method of claim 29 further comprising adding one or more additives to the vessel.

31. The method of claim 29 comprising controlling the temperature in the vessel.

32. The method of claim 29 further comprising monitoring one or more electrochemical properties of the fluid in the vessel.

33. A method for monitoring for damage to a metal sample comprising:

(a) applying a physical stress to a metal sample;

(b) placing the metal sample under stress into a sealed vessel;

(c) adding one or more fluids to the vessel;

(d) measuring the strain on the metal sample over a specified time interval;

(e) controlling the environment inside the vessel;

(f) calculating the rate of change of the strain measurement over the specified time interval;

(g) recording the rate of change of the strain measurement;

(h) calculating a moving average of two or more previously recorded rates of change of the strain measurement;

(i) monitoring the moving average to detect damage to the metal sample;

(j) monitoring one or more electrochemical properties of the fluid in the vessel; and (k) correlating changes in the electrochemical properties of the fluid with changes in the moving average of the strain measurement to determine electrochemical indicators of damage to the metal sample.

34. The method of claim 33 further comprising adding one or more additives to the vessel.

35. The method of claim 33 further comprising controlling the temperature in the vessel.

36. A method for monitoring for damage to a metal sample comprising:

(a) applying a physical stress to a metal sample;

(b) placing the metal sample under stress into a sealed vessel;

(c) adding one or more fluids to the vessel;

(d) measuring the strain on the metal sample over a specified time interval;

(e) controlling the environment inside the vessel;

(f) controlling the temperature in the vessel;

(g) calculating the rate of change of the strain measurement over the specified time interval;
(h) recording the rate of change of the strain measurement;
(i) calculating a moving average of two or more previously recorded rates of change of the strain measurement;
(j) monitoring the moving average to detect damage to the metal sample; and
(k) monitoring one or more electrochemical properties of the fluid in the vessel.

* * * * *